(12) United States Patent
Diller et al.

(10) Patent No.: US 7,058,998 B2
(45) Date of Patent: Jun. 13, 2006

(54) FOOT CONTROL (75) Inventors: Mark G. Diller, Clayton, OH (US); Randall H. Evers, Osgood, OH (US)

(73) Assignee: Midmark Corporation, Versailles, OH (US)

( * ) Notice: Subject to any disclaimer, the term of this patent is extended or adjusted under 35 U.S.C. 154(b) by 23 days.

(21) Appl. No.: 10/814,974

(22) Filed: Mar. 31, 2004

(65) Prior Publication Data

US 2005/0172404 A1  Aug. 11, 2005

Related U.S. Application Data (60) Provisional application No. 60/542,753, filed on Feb. 6, 2004.

(51) Int. Cl.
G05G 1/14 (2006.01)
A61G 13/02 (2006.01)

(52) U.S. Cl. .................... 5/614; 5/616; 74/560; 74/512

(58) Field of Classification Search .................... 5/614, 5/616; 74/512, 560; 200/86.5, 512, 517, 200/280–281
See application file for complete search history.

(56) References Cited

U.S. PATENT DOCUMENTS

| | | | |
|---|---|---|---|
| 4,041,609 A | 8/1977 | Bresnahan et al. | 32/22 |
| 4,114,275 A | 9/1978 | Jones et al. | 32/22 |
| 4,558,194 A | 12/1985 | Wiblin | 200/61.89 |
| 4,586,398 A | 5/1986 | Yindra | 74/512 |
| 4,676,750 A | 6/1987 | Mason | 433/101 |
| 4,956,592 A | 9/1990 | Schulte et al. | 318/560 |
| D319,158 S | 8/1991 | Jones et al. | D6/491 |
| 5,300,926 A | 4/1994 | Stoeckl | 345/157 |
| 5,340,953 A * | 8/1994 | Krebs et al. | 200/86.5 |
| 5,423,231 A | 6/1995 | Helfrich et al. | 74/561 |
| 5,467,002 A | 11/1995 | Brooks | 318/553 |
| D379,349 S | 5/1997 | Nichols et al. | D13/167 |
| 5,712,460 A * | 1/1998 | Carr et al. | 200/86.5 |
| 6,054,831 A * | 4/2000 | Moore et al. | 318/581 |
| 6,212,713 B1 | 4/2001 | Kuck et al. | 5/617 |
| D450,661 S | 11/2001 | Weisz et al. | D13/167 |
| D463,381 S | 9/2002 | Westermann | D13/167 |
| 6,866,507 B1 * | 3/2005 | Beerstecher | 433/101 |
| 2005/0172404 A1 | 8/2005 | Diller et al. | 5/616 |

\* cited by examiner

*Primary Examiner*—Michael Trettel
(74) *Attorney, Agent, or Firm*—Wood, Herron & Evans, LLP (57) ABSTRACT A foot control for controlling power-driven functions of a medical apparatus which positions a patient in a variety of examination and treatment positions. The foot control includes a membrane switch and a flexible keypad overlying the membrane switch. The flexible keypad is configured to actuate switch elements of the membrane switch in response to selective pressure applied on the keypad by a user's foot. Different configurations of keypads are interchangeable on the foot control to change the control functionality of the foot control while the membrane switch remains unchanged.

30 Claims, 7 Drawing Sheets

FOOT CONTROL

The present application claims the filing benefit of pending U.S. Provisional Application Ser. No. 60/542,753, filed Feb. 6, 2004, the disclosure of which is hereby incorporated herein by reference in its entirety.

CROSS REFERENCE

The present application is related to U.S. Ser. No. 29/199,010, entitled Foot Control and U.S. Ser. No. 29/199,011, entitled Foot Control, filed on even date herewith.

FIELD OF THE INVENTION

The present invention relates generally to medical apparatus for positioning a patient in a variety of examination and treatment positions and, more particularly, to a foot control for use with such medical apparatus to control various power-driven functions of the medical apparatus.

BACKGROUND OF THE INVENTION

Power operated examination tables are well known in the art for positioning a patient in a variety of examination and treatment positions such as, for example, the Trendelenburg position, reverse Trendelenburg position, urological examination position, proctological examination position, chair position and horizontal table position. The examination tables have power-driven actuators connected to patient support sections of the table, such as a seat section, back section and leg and foot support section, so that the sections can be moved to desired positions to place the patient in the necessary work position for the examination or treatment procedure. Following the procedure, the examination table is returned to a patient entry/exit chair position which enables a patient to comfortably exit the examination table and the table is now properly positioned to receive the next patient.

Typically, power-driven examination tables include a foot control which allows a doctor, nurse or attendant to control power-driven functions of the table to position the table in a variety of positions. Ordinarily, the foot control has a number of pedals which may be depressed or rocked by foot action to energize the actuators for moving the table into the desired position. The use of a foot control is advantageous in that it allows the table to be positioned while maintaining a sterile field, and the desired table position can be set or adjusted without requiring shifting of the doctor's hands or eyes away from the area of examination or treatment.

Foot controls which incorporate separate pedals for controlling the power-driven functions of the examination table are susceptible, in use, to certain problems. Typically, such foot controls require a doctor to actuate different pedals which are spaced from each other so that the doctor's foot must be lifted, shifted and then placed upon the various pedals to actuate the various power-driven functions of the table. During a treatment or examination procedure, the doctor may lose orientation of the doctor's foot in relation to the pedals as the doctor moves around so that the doctor may accidently depress the wrong pedal for the intended movement of the examination table.

Also, manufacturers of examination tables typically supply various models of tables with each model offering different power-driven functions for positioning of the table. Additionally, customers may purchase different options for the same model of examination table so that the same model of table may be configured by the supplier with different power-driven function capabilities. In the past, examination table suppliers have been required to design and manufacture different configurations of foot controls for the various power-driven functions offered with the examination tables. This increases the engineering development and manufacturing costs for the examination table supplier.

Therefore, there is a need for a foot control which minimizes the risk for accidental actuation by a doctor, nurse or attendant of an unintended power-driven function of a medical apparatus. There is also a need for a foot control which is readily adaptable to various configurations of a medical apparatus having different power-driven function capabilities.

SUMMARY OF THE INVENTION

The present invention overcomes the foregoing and other shortcomings and drawbacks of foot controls heretofore known for controlling power-driven functions of a medical apparatus to position a patient in a variety of examination and treatment positions. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, a foot control is provided for use with medical apparatus, such as an examination table by way of example, having multiple power-driven functions to position a patient supported thereupon in a variety of examination and treatment positions. According to one aspect of the present invention, the foot control includes a base which is adapted to be supported on a floor surface and a membrane switch supported by the base. The membrane switch has multiple switch elements which are operable, when actuated, to control the power-driven functions of the medical apparatus.

According to another aspect of the present invention, a flexible keypad is mounted on the foot control to overlie the membrane switch. The keypad has actuation keys which protrude upwardly from the keypad so as to be depressible by a user's foot. Each of these actuation keys is positioned generally in registry with its associated switch element and is configured to actuate its associated switch element in response to selective pressure applied on the actuation keys by a user's foot. Switch actuators extend from inner surfaces of the keypad actuators and toward the membrane switch so that the switch actuators contact, but do not actuate in a relaxed state, the switch elements which are generally in registry with the switch actuators.

In accordance with another aspect of the present invention, the keypad and the membrane switch define a pair of independent operating stations on the foot control which are responsive to selective pressure applied on the keypad by a user's foot. Each of the operating stations is configured to control two independent power-driven functions of the medical apparatus. In one embodiment, each of the first and second operating stations is configured to control two reversible power-driven functions of the medical apparatus. The pair of operating stations are particularly oriented so that a user is able to easily actuate the power-driven functions controlled by the pair of operating stations simply by pivoting the user's foot about its heel. This minimizes the risk that a user will lose orientation of the user's foot relative to the foot control which may otherwise occur if a user is required to lift, shift and place the user's foot on the foot control to actuate the power-driven functions of the medical apparatus. Each operating station further permits a user to simultaneously actuate two of the power-driven functions provided at each of the operating stations by selectively applying pressure to two of the actuation keys at the same time.

In accordance with another aspect of the present invention, the flexible keypad is interchangeable with one or more other keypads having a different configuration for actuating the actuation keys so that the control functionality of the foot control can be changed while the membrane switch remains unchanged. In this way, a common membrane switch can be provided for the foot control, and the keypads can be easily interchanged and mounted on top of the foot control to provide different options for controlling the power-driven functions of the medical apparatus. One keypad may be mounted on the foot control to provide control of all of the available power-driven functions of the medical apparatus while a differently configured keypad may be mounted on the foot control to provide control of less than all of the available power-driven functions of the medical apparatus. In this way, the foot control can be readily configured for controlling different capabilities of the same model of medical apparatus purchased by customers or to configure the foot control for controlling different models of the medical apparatus having different power-driven function capabilities. In either situation, the membrane switch remains unchanged and only the configuration of the keypad needs to be changed for the particular application.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENT

Referring to the drawings, and to FIGS. 7–12 in particular, an exemplary examination table 10 is shown which includes a power-operated telescoping base 12 for supporting the examination table 10 above a floor surface. The base 12 supports a seat section 14a, back section 14b, foot and leg support section 14c, and headrest section 14d which define an adjustable patient support surface 16 for supporting a patient in a variety of examination and treatment positions. The seat section 14a, back section 14b and foot and leg support section 14c are all hingedly connected and may be adjusted under power into multiple work positions which may be selected in accordance with the particular procedure being performed and the particular preferences of the chair operator or doctor. The telescoping base 12 of the exemplary examination table 10 may be extended or retracted under power to raise and lower the seat section 14a, and the seat section 14a may be adjusted into rearwardly and forwardly tilted positions in a range between about 0° and about 30° relative to a horizontal plane parallel to the floor as may be desired when the examination table 10 is configured into a Trendelenburg or reverse Trendelenburg position.

In one embodiment, the patient support surface 16 of the seat section 14a travels in a range from about 19 inches from the floor to about 40 inches from the floor. This range of movement provides a safe and comfortable entry/exit position for a patient when the base 12 is lowered and a convenient position for a doctor to examine or treat the patient when the base 12 is raised.

Figure 8:
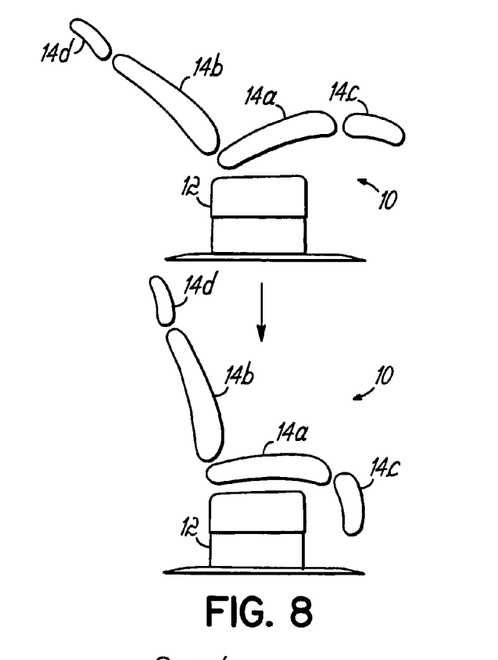
Figure 12:
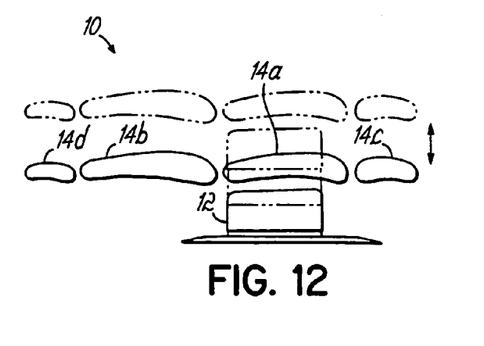

The back section 14b travels in a range between about 0° and about 85° relative to a horizontal plane parallel to the floor and the foot and leg support section 14c travels in a range between about 0° and about 90° relative to a horizontal plane parallel to the floor. Of course, other ranges of movements of the seat section 14a, back section 14b and foot and leg support section 14c are possible as well. The exemplary examination table 10 is therefore adjustable to support a patient in a variety of work positions, including a supine position as shown in FIG. 12 and a generally upright sitting position as shown in FIG. 8 which may be used when a patient is entering or exiting the examination table 10.

The power-driven functions of the examination table 10 are provided by four reversible actuators (FIG. 6) including a base actuator 18a, a back actuator 18b, a tilt actuator 18c and a foot actuator 18d which are electrically coupled to a controller 20 of the examination table 10 and operably connected to the sections 14a–c of the examination table 10. System transformers 22 (FIG. 6) are electrically coupled to the controller 20 to energize the actuators 18a–d when the examination table 10 is being adjusted to a desired work position. The mounting of the actuators 18a–d within the examination table 10 is not shown in the drawings as their operation is well known in the art. For a more detailed description of the mounting and operation of such actuators, the reader is referred to U.S. Pat. Nos. 4,956,592 and 6,212,713, owned by the common assignee, which are hereby incorporated herein by reference. The actuators 18a–d may comprise electric actuators, hydraulic actuators or other suitable type of powered motion actuators well known in the art. Controls for the actuators 18a–d are provided by switches mounted in a hand control 24 and a foot control 26 which are each electrically coupled to the controller 20. As will be described in greater detail below, the hand and foot controls 24, 26 provide the doctor, nurse, or attendant the ability to control the power-driven functions of the examination table 10 to position a patient between a generally upright sitting position and a desired work position. While the present invention will be described in detail below in connection with the exemplary examination table 10, it will be appreciated that the foot control 26 of the present invention may be used in combination with other types of power-driven multi-position tables, chairs and examination/treatment apparatus without departing from the spirit and scope of the present invention.

Figure 1:
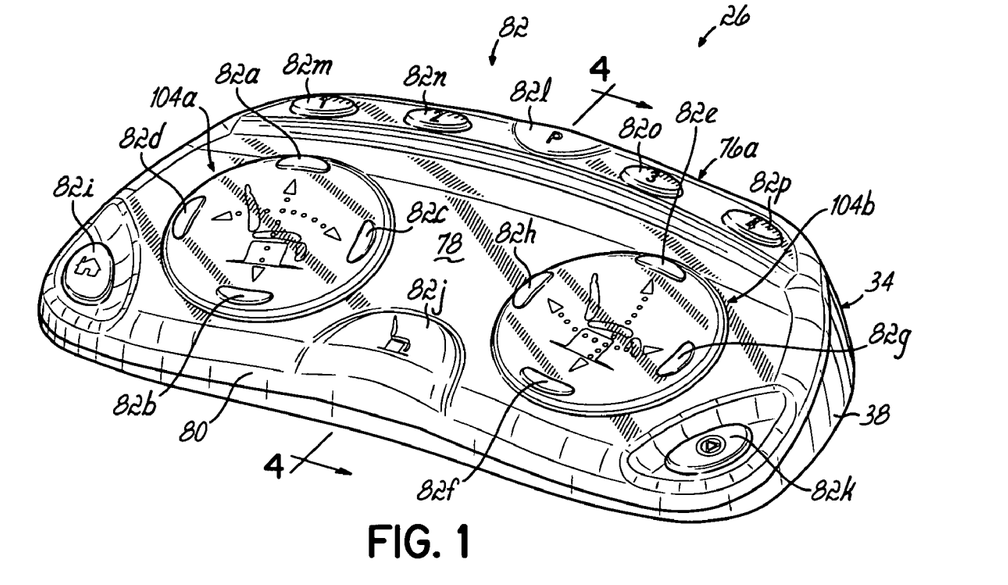
FIG. 1 is a perspective view of a foot control in accordance with the principles of the present invention.
Figure 2:
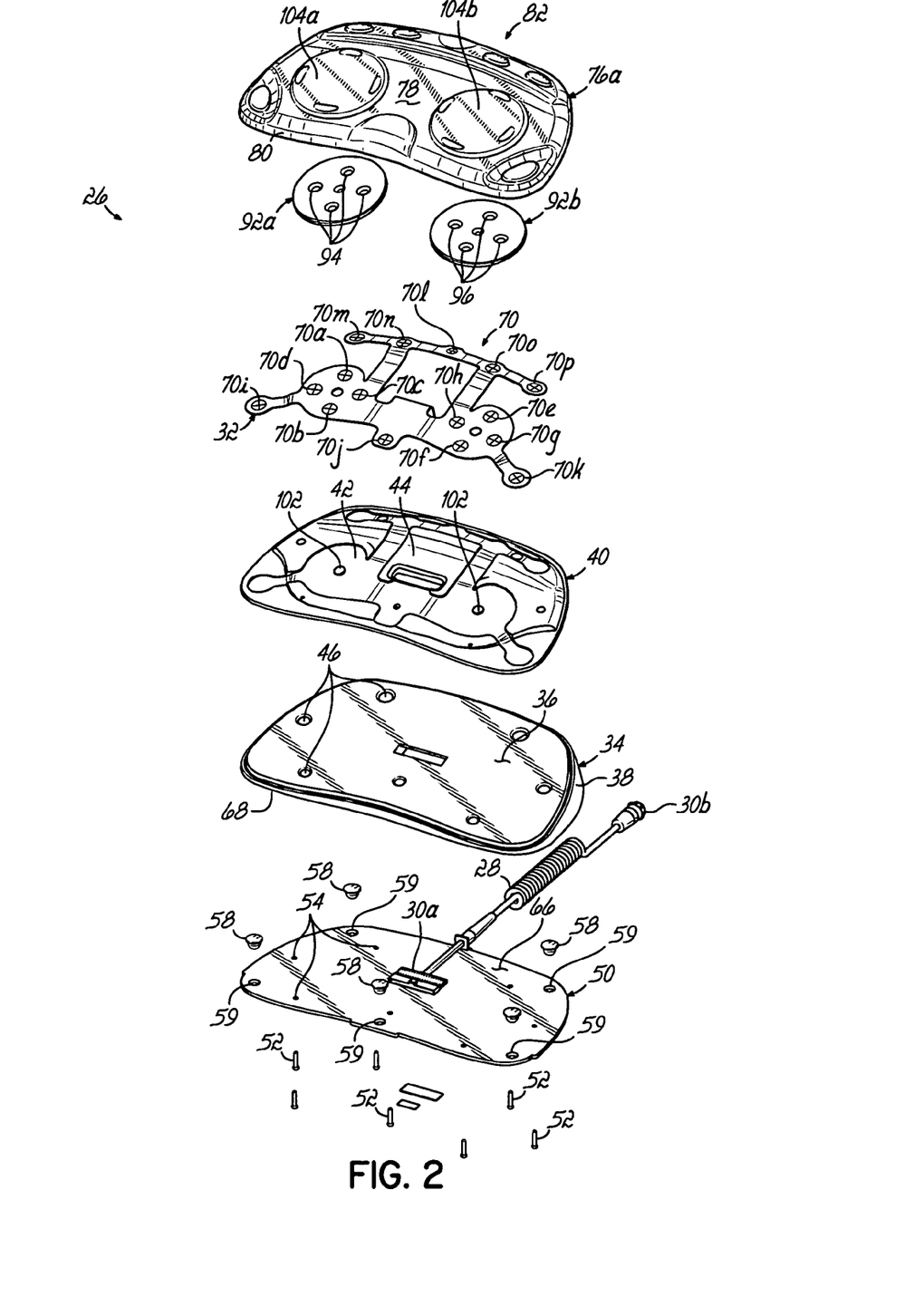
FIG. 2 is an exploded perspective view of the foot control shown in FIG. 1.
Figure 3:
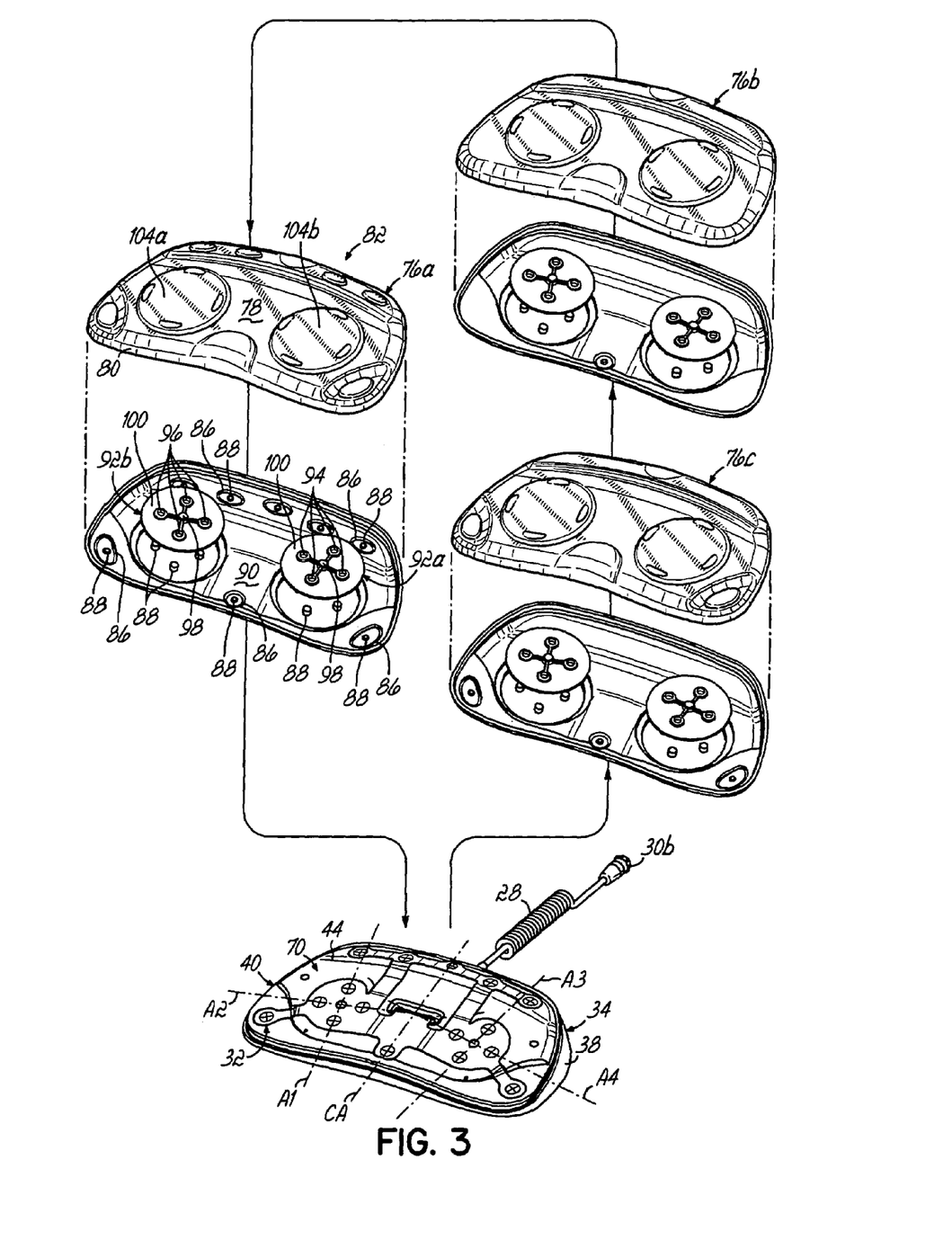
FIG. 3 is a perspective view of the foot control shown in FIG. 1, illustrating interchangeable keypads for use with the foot control in accordance with principles of the present invention.
Figure 4:
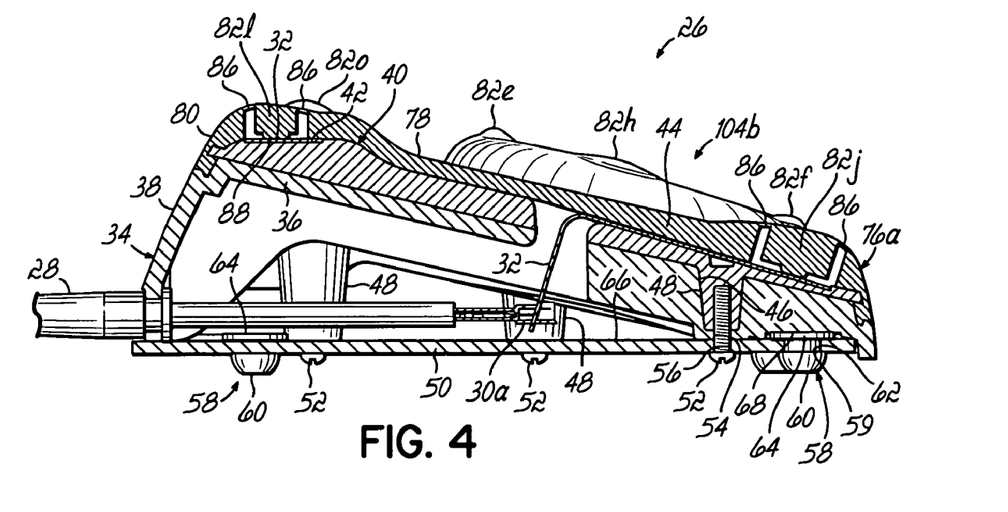
FIG. 4 is a cross-sectional view taken along line 4—4 of FIG. 1.

The foot control 26 is the focus of the present invention and is shown in FIGS. 1–6 and 13. According to one aspect of the present invention, the foot control 26 is electrically coupled to the controller 20 through an electrical cable 28 (FIGS. 2–4). The cable 28 has a pair of connectors 30a, 30b provided at its opposite ends which are configured to connect to the base 12 of the examination table 10 and to a membrane switch 32 which is mounted within the foot control 26 as will be described in greater detail below. As shown in FIGS. 2 and 4, the foot control 26 has a base portion 34 which includes an upwardly and rearwardly inclined top wall 36 and a supporting side wall 38 depending from the top wall 36. A retainer portion 40 is supported on the top wall 36 of the base portion 34 and has a recess 42 formed in a top wall 44 thereof which is configured to retain the membrane switch 32 in a fixed position on the top wall 44 of the retainer portion 40. The base portion 34 of the foot control 26 has tubular cavities 46 which are configured to receive tubular posts 48 extending downwardly from the top wall 44 of the retainer portion 40 so as to properly align the retainer portion 40 with the base portion 34 during assembly of the foot control 26.

As shown in FIGS. 2 and 4, a base plate 50 is mounted beneath the base portion 34 of the foot control 26 through fasteners 52 which extend through apertures 54 formed in the base plate 50 and apertures 56 formed in the base portion 34 which communicate with the tubular cavities 46. The fasteners 52 threadably engage the tubular posts 48 of the retainer portion 40 to secure the base plate 50, base portion 34 and retainer portion 40 as an assembly. The base plate 50 has sufficient weight to minimize movement of the foot control 26 on the floor when the foot control 26 is operated as will be described in detail below.

To further minimize undesirable movement of the foot control 26, rubber foot members 58 are mounted to the base plate 50 to provide a frictional contact with the floor. Each of the foot members 58 is mounted within an aperture 59 formed in the base plate 50. The foot members 58 include an outer head portion 60 which has a diameter greater than the diameter of the apertures 59 formed in the base plate 50. A stem portion 62 of the foot members 58 extends through the apertures 59 of the base plate 50 and terminates in a radially outwardly directed annular flange portion 64. The annular flange portions 64 of the foot members 58 also have a diameter greater than the diameter of the apertures 59 formed in the base plate 50 and are configured of sufficient extent to essentially prevent the foot members 58 from being pulled out of the apertures 59 during normal use of the foot control 26. In one embodiment, as shown in FIG. 4, the diameter of the annular flange portions 64 is greater than the diameter of the outer head portions 60 so that, during assembly of the foot control 26, the foot members 58 are engaged with the base plate 50 by passing the outer head portions 60 through the apertures 59 so as to capture the base plate 50 between the outer head portions 60 and the annular flange portions 64.

To further prevent disengagement of the foot members 58 from the base plate 50 during use of the foot control 26, the annular flange portions 64 of the foot members 58 are clamped between an upper surface 66 of the base plate 50 and a lower surface 68 of the base portion 34 as shown in FIG. 4. In this way, the foot members 58 are reliably secured to the foot control 26 and are not likely to disengage from the base plate 50 during normal use of the foot control 26.

Figure 13:
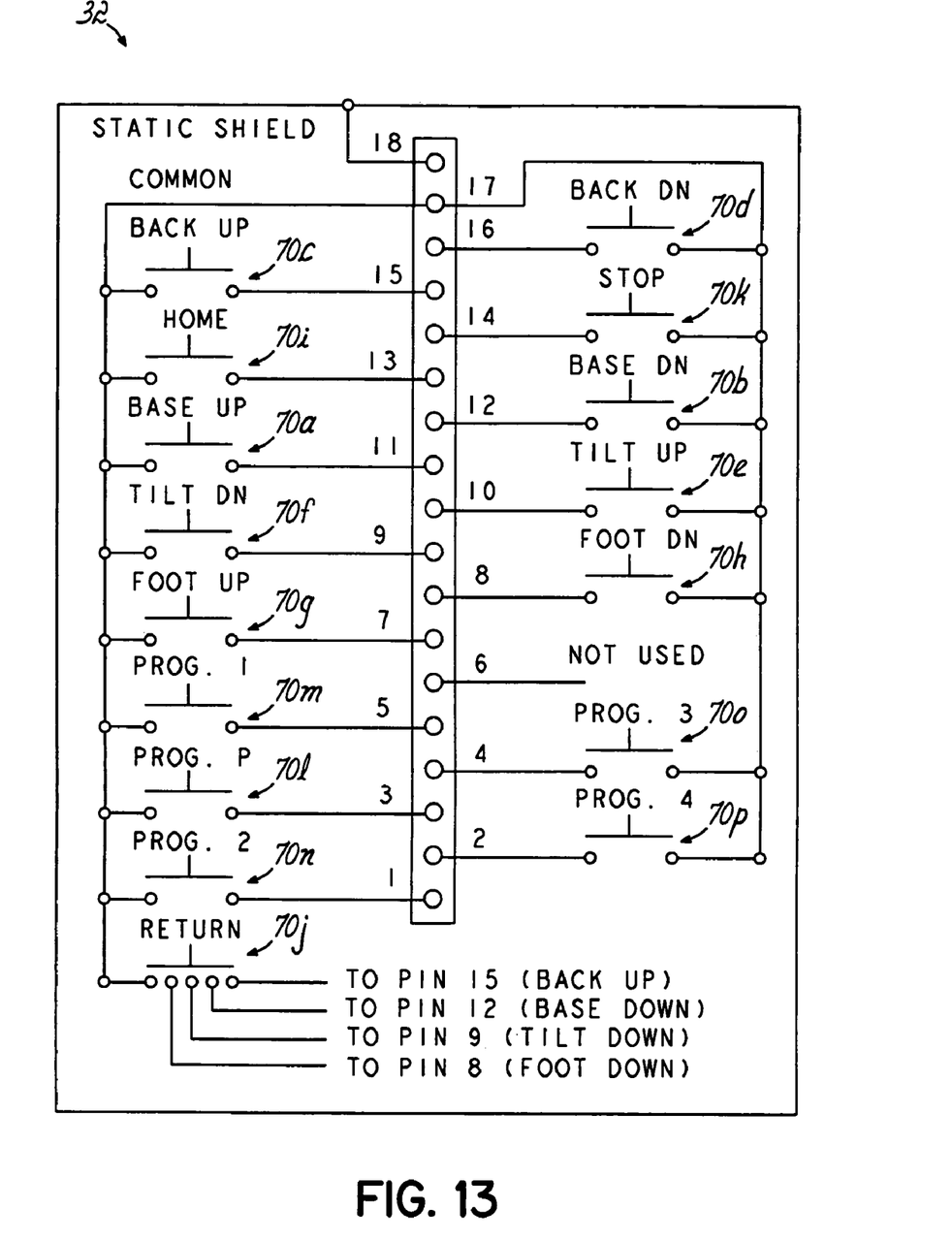
FIG. 13 is a schematic diagram of one embodiment of the foot control of the present invention.

In accordance with another aspect of the present invention, as shown in FIGS. 2 and 13, the membrane switch 32 has multiple switch elements 70 to control the power-driven functions of the examination table 10 in response to selective actuation of the switch elements 70 as described in greater detail below. In one embodiment, the membrane switch 32 includes a "BASE UP" switch element 70a, a "BASE DOWN" switch element 70b, a "BACK UP" switch element 70c, a "BACK DOWN" switch element 70d, a "TILT UP" switch element 70e, a "TILT DOWN" switch element 70f, a "FOOT UP" switch element 70g, a "FOOT DOWN" switch element 70h, a "HOME" switch element 70i, a "CHAIR RETURN" switch element 70j, a "STOP" switch element 70k, a "PROGRAM" switch element 70l and "POSITION" switch elements 70m–p.

Figure 9:
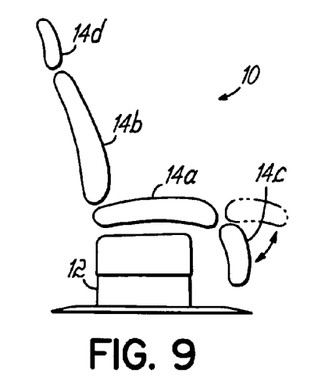
Figure 10:
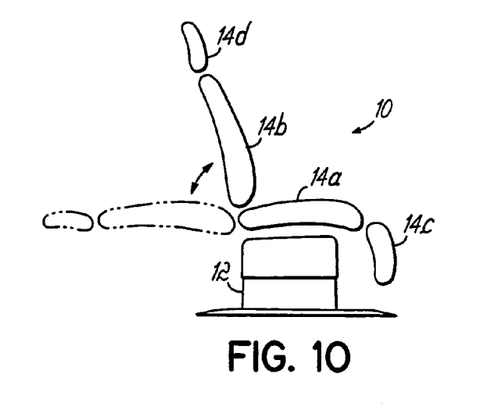
Figure 11:
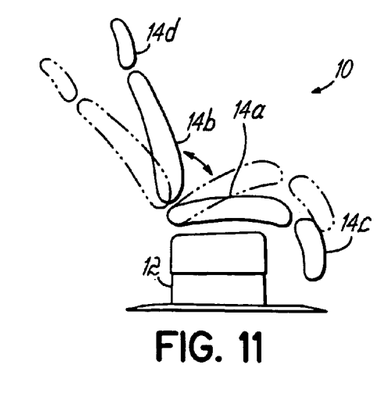

The "BASE UP" and "BASE DOWN" switch elements 70a, 70b, when actuated, control reversible movement of the base actuator 18a to raise and lower the seat section 14a as shown in FIG. 12. The "BACK UP" and "BACK DOWN" switch elements 70c, 70d, when actuated, control reversible movement of the back actuator 18b to raise and lower the back section 14b as shown in FIG. 10. The "TILT UP" and "TILT DOWN" switch elements 70e, 70f, when actuated, control reversible movement of the tilt actuator 18c to rearwardly and forwardly tilt the seat section 14a as shown in FIG. 11. The "FOOT UP" and "FOOT DOWN" switch elements 70g, 70h, when actuated, control reversible movement of the foot actuator 14d to raise and lower the foot and leg support section 14c as shown in FIG. 9.

Figure 6:
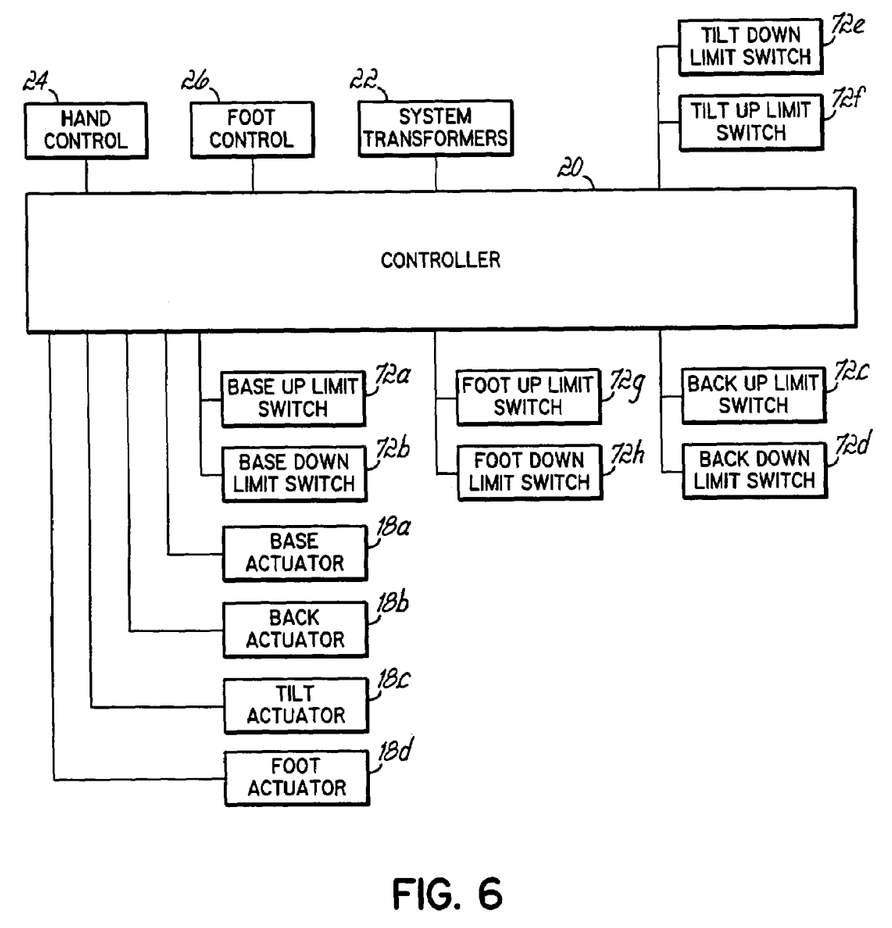
FIG. 6 is a functional block diagram of an exemplary control system for an examination table incorporating the foot control of the present invention.

In one embodiment, each of the switch elements 70a–h is a "momentary" switch such that the power-driven functions controlled by these switch elements are performed only when the switch elements 70a–h are held in an actuated state. The power-driven functions controlled by these switch elements 70a–h are stopped when the switch elements are opened, the minimum or maximum allowable positions of the seat section 14a, back section 14b and foot and leg support section 14c are reached, or the "STOP" switch element 70k is actuated. As shown in FIG. 6, "BASE UP" and "BASE DOWN" limit switches 72a, 72b, "BACK UP" and "BACK DOWN" limit switches 72c, 72d, "TILT UP" and "TILT DOWN" limit switches 72e, 72f and "FOOT UP" and "FOOT DOWN" limit switches 72g, 72h are electrically coupled to the controller 20 and set the allowable minimum and maximum positions of the examination table 10.

Figure 7:
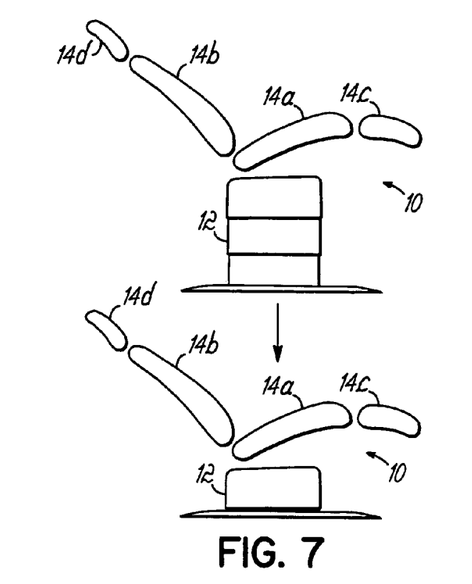
FIGS. 7–12 are diagrammatic views showing various power-driven functions of the exemplary examination table which are controlled by the foot control of the present invention.

As shown in FIG. 7, the "HOME" switch element 70i, when actuated, controls movement of the base actuator 18a to lower the examination table 10 from a raised position. The "HOME" switch element 70i allows a doctor, nurse or attendant to lower the examination table 10 from a work position without otherwise changing the configuration of the examination table 10. In one embodiment, the "HOME" switch element 70i is a "maintaining" switch such that the power-driven function controlled by this switch element is performed by a single actuation of the switch element 70i to lower the examination table 10 to about 23 inches from the floor. If the "HOME" switch element 70i is actuated and temporarily held in the actuated state, the examination table 10 is lowered to about 19 inches from the floor. Downward movement of the examination table 10 is stopped when the "HOME" position is reached or the "STOP" switch element 70k is actuated.

As shown in FIG. 8, the "CHAIR RETURN" switch element 70j, when actuated, controls simultaneous movement of the base actuator 18a, back actuator 18b, tilt actuator 18c and foot actuator 18d to return the examination table 10 from a work position to a chair position whereat the patient is supported in a generally upright sitting position. The "CHAIR RETURN" switch element 70j allows a doctor, nurse or attendant to automatically change the configuration of the examination table 10 from a work position to the chair position so that a patient may comfortably enter or exit the examination table 10 before or following an examination or treatment procedure. In one embodiment, the "CHAIR RETURN" switch element 70j is a "momentary" switch such that the power-driven functions controlled by this switch element are performed only when the switch element 70j is held in an actuated state. The power-driven functions controlled by the switch element 70j are stopped when the switch element is opened, the chair position is reached, or the "STOP" switch element 70k is actuated.

The "PROGRAM" switch element 70l and the "POSITION" switch elements 70m–p allow a doctor, nurse or attendant to program and recall frequently used positions of the examination table 10. To program a position, the examination table 10 is first adjusted to a desired work position. The "PROGRAM" switch element 70l is then actuated followed by actuation of one of the "POSITION" switch elements 70m–p to store the set position of the examination table 10 for later recall. Four "POSITION" switch elements 70m–p are provided to store and recall four different examination table positions. To recall a programmed position, the user actuates one of the "POSITION" switch elements 70m–p which, when actuated, controls movement of the base actuator 18a, back actuator 18b, tilt actuator 18c and foot actuator 18d to move the examination table 10 to the stored work position. In one embodiment, the "POSITION" switch elements 70m–p are "momentary" switches such that the power-driven functions controlled by these switch elements are performed only when the switch elements 70m–p are held in an actuated state. The power-driven functions controlled by the switch element 70m–p are stopped when the switch elements 70m–p are opened, the programmed position is reached, or the "STOP" switch element 70k is actuated.

Figure 5:
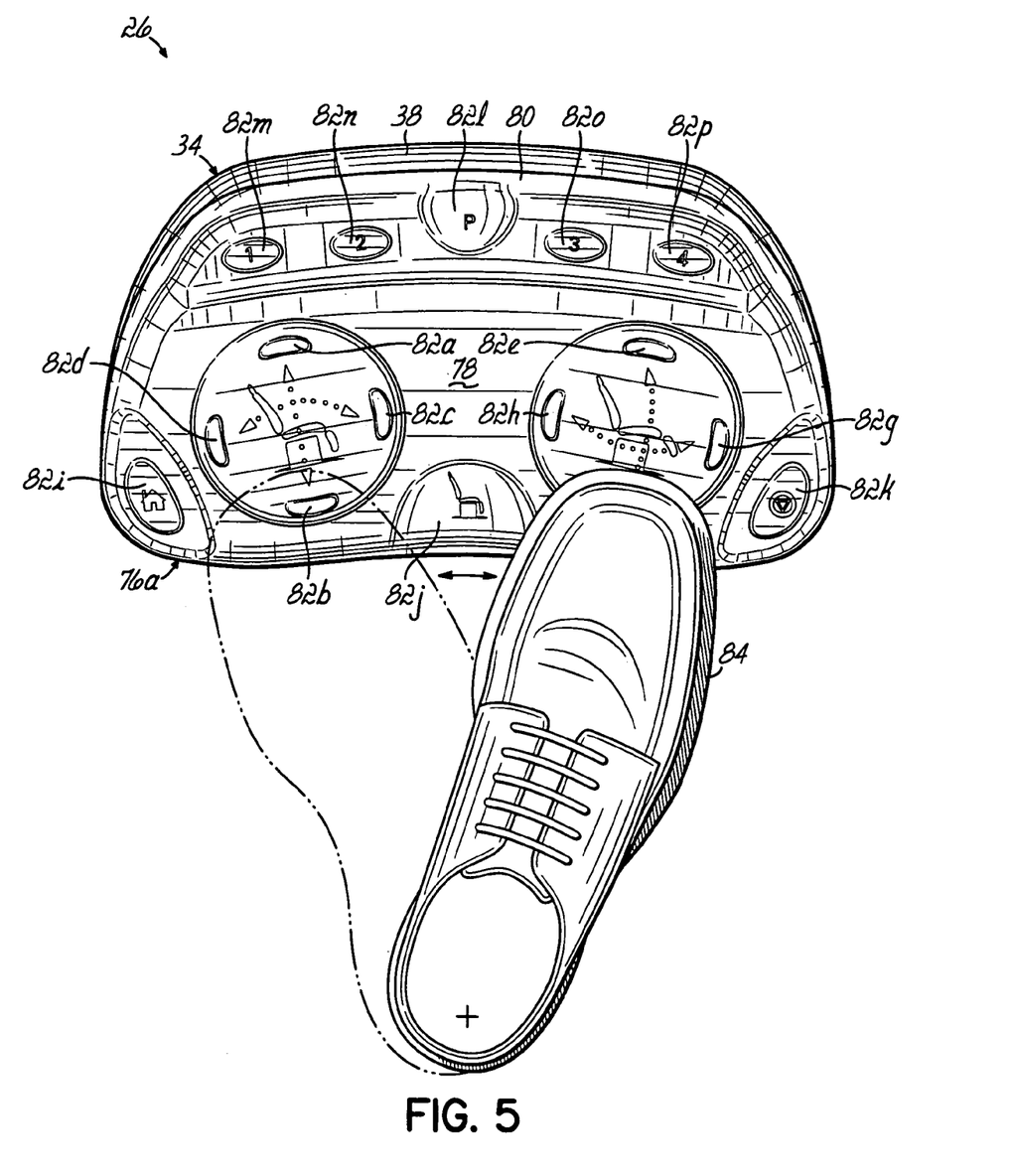
FIG. 5 is a top plan view of the foot control shown in FIG. 1, illustrating its method of operation.

In accordance with another aspect of the present invention, the multiple switch elements 70 are actuated through a flexible keypad 76a which is positioned to overlie the switch elements 70 as shown in FIGS. 1–5. In one embodiment, the keypad 76a is compression molded from silicone material, although other suitable flexible materials are possible as well. The keypad 76a has a top wall 78 and a side wall 80 depending from the top wall 78. The side wall 80 of the keypad 76a is configured to engage and form a seal with the base portion 34 and retainer portion 40 of the foot control 26 as best seen in FIG. 4. In one embodiment, the keypad 76a has actuation keys 82 which protrude upwardly from the keypad 76a so as to be depressible by a user's foot 84 as shown in FIG. 5. The actuation keys 82 of keypad 76a include a "BASE UP" actuation key 82a, a "BASE DOWN" actuation key 82b, a "BACK UP" actuation key 82c, a "BACK DOWN" actuation key 82d, a "TILT UP" actuation key 82e, a "TILT DOWN" actuation key 82f, a "FOOT UP" actuation key 82g, a "FOOT DOWN" actuation key 82h, a "HOME" actuation key 82i, a "CHAIR RETURN" actuation key 82j, a "STOP" actuation key 82k, a "PROGRAM" actuation key 82l and "POSITION" actuation keys 82m–p. Each of these actuation keys 82a–p is positioned in general registry with its associated switch element 70a–p and is configured to actuate its associated switch element 70a–p in response to selective pressure applied on the actuation keys 82a–p by a user's foot 84.

In one embodiment, as shown in FIGS. 3 and 4, each of the actuation keys 82i–p is connected to the top wall 78 of the keypad 76a through a generally thin annular web 86 which permits movement of the actuation keys 82i–p relative to the top wall 78 of the keypad 76a when the key actuators 82i–p are depressed by a user's foot 84. A switch actuator 88 (FIG. 3) extends from an inner surface 90 of each of the keypad actuators 82a–p and toward the membrane switch 32 so that the switch actuators 88 contact, but do not actuate in a relaxed state, the switch elements 70a–p which are in general registry with the switch actuators 88. In one embodiment, the switch actuators 88 are integrally molded with the keypad 76a from a flexible material such as silicone.

In one embodiment, a pair of stiffener members 92a and 92b are adhered or otherwise attached to the inner surface 90 of the keypad 76a as shown in FIG. 3. The stiffener member 92a has four apertures 94 which allow the switch actuators 88 associated with the "BASE UP", "BASE DOWN", "BACK UP" and "BACK DOWN" actuation keys 82a–d to extend therethrough and contact their associated "BASE UP", "BASE DOWN", "BACK UP" and "BACK DOWN" switch elements 70a–d. Similarly, the stiffener member 92b has four apertures 96 which allow the switch actuators 88 associated with the "TILT UP", "TILT DOWN", "FOOT UP" and "FOOT DOWN" actuation keys 82e–h to extend therethrough and contact their associated "TILT UP", "TILT DOWN", "FOOT UP" and "FOOT DOWN" switch elements 70e–h.

As shown in FIGS. 2–3, each of the stiffener members 92a, 92b has a centrally located boss 98 which extends downwardly from a lower surface 100 of the stiffener members 92a, 92b. The bosses 98 of the stiffener members 92a, 92b engage upwardly extending bosses 102 formed in the recess 42 of the foot control retainer portion 40 so that the stiffener members 92a, 92b are mounted to pivot or tilt in response to selective pressure applied to the "BASE UP", "BASE DOWN", "BACK UP", "BACK DOWN", "TILT UP", "TILT DOWN", "FOOT UP" and "FOOT DOWN" actuation keys 82a–h by a user's foot.

In one embodiment, the "BASE UP", "BASE DOWN", "BACK UP", "BACK DOWN", "TILT UP", "TILT DOWN", "FOOT UP" and "FOOT DOWN" actuation keys 82a–h of keypad 76a and the "BASE UP", "BASE DOWN", "BACK UP", "BACK DOWN", "TILT UP", "TILT DOWN", "FOOT UP" and "FOOT DOWN" switch elements 70a–h define a pair of operating stations 104a and 104b on the foot control 26. Operating station 104a provides control of the "BASE UP", "BASE DOWN", "BACK UP" and "BACK DOWN" power-driven functions of the examination table 10 and operating station 104b provides control of the "TILT UP", "TILT DOWN", "FOOT UP" and "FOOT DOWN" power-driven functions of the examination table 10. Each operating station 104a, 104b comprises a circular disk which protrudes upwardly from the keypad 76a and is connected to the top wall 78 of the keypad 76a through a generally thin annular web (not shown).

As shown in FIG. 3, the "BASE UP" and "BASE DOWN" switch elements 70a–b are aligned on an axis "A1" and the "BACK UP" and "BACK DOWN" switch elements 70c–d are aligned on a transverse axis "A2". The "TILT UP" and "TILT DOWN" switch elements 70e–f are aligned on an axis "A3" and the "FOOT UP" and "FOOT DOWN" switch elements 70g–h are aligned on an axis "A4".

In accordance with another aspect of the present invention, the axes "A1" and "A3" intersect a central axis "CA" of the foot control 26. In this way, the operating stations 104a, 104b are oriented so that a user is able to easily actuate the power-driven functions controlled by the pair of operating stations 104a, 104b simply by pivoting the user's foot 84 about its heel as shown in FIG. 5. This minimizes the risk that a user will lose orientation of the user's foot relative to the foot control 26 which may otherwise occur if a user is required to lift, shift and place the user's foot on the foot control to actuate the power-driven functions of the examination table 10. Each operating station 104a, 104b further permits a user to simultaneously actuate two of the power-driven functions provided at each of the operating stations 104a, 104b by selectively applying pressure to two of the actuation keys 82 at the same time.

In accordance with another aspect of the present invention, as shown in FIG. 3, the flexible keypad 76a is interchangeable with one or more keypads 76b, 76c having a different configuration for actuating the actuation keys 82 so that the control functionality of the foot control 26 can be changed while the membrane switch 32 remains unchanged. For example, the keypad 76b does not include the "PROGRAM" actuation key 82l and "POSITION" actuation keys 82m–p for actuating the "PROGRAM" switch element 70l and the "POSITION" switch elements 70m–p. The keypad 76c does not include the "PROGRAM" actuation key 82l and "POSITION" actuation keys 82m–p for actuating the "PROGRAM" switch element 70l and the "POSITION" switch elements 82m–p, the "HOME" actuation key 82i for actuating the "HOME" switch element 70i and the "STOP" actuation key 82k for actuating the "STOP" switch element 70k.

In this way, a common membrane switch 32 can be provided for the foot control 26, and the keypads 76a, 76b and 76c can be easily interchanged and mounted on top of the foot control 26 to provide different options for controlling the power-driven functions of the examination table 10. One keypad 76a may be mounted on the foot control 26 to provide control of all of the available power-driven functions of the examination table 10 while another keypad 76b, 76c may be mounted on the foot control 26 to provide control of less than all of the available power-driven functions of the table. This is advantageous to configure the foot control 26 for controlling different capabilities of the same model of examination table 10 purchased by customers or to configure the foot control 26 for controlling different models of the examination table 10 having different power-driven function capabilities. In either situation, the membrane switch 32 remains unchanged and only the configuration of the keypad 76a–c needs to be changed for the particular application.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicants' general inventive concept.

Having described the invention, what is claimed is:

1. A foot control for use with medical apparatus having multiple power-driven functions to position a patient supported thereupon in multiple work positions, comprising:
   a base adapted to be supported on a surface;
   a membrane switch supported by said base and having a plurality of switch elements, each of said switch elements being operable, when actuated, to control at least one of the power-driven functions of the medical apparatus; and
   a flexible keypad overlying said membrane switch and having a plurality of switch actuators extending from said keypad toward said membrane switch, each of said switch actuators being generally in registry with a respective one of said plurality of switch elements to actuate said switch element in response to selective pressure applied on said keypad by a user's foot,
   wherein said keypad is configured to simultaneously actuate a pair of said switch elements in response to selective pressure applied on said keypad by a user's foot so as to simultaneously control two independent power-driven functions of the medical apparatus upon actuation of said pair of switch elements.

2. The foot control of claim 1 wherein said keypad and said plurality of switch actuators are integrally molded from a flexible material.

3. The foot control of claim 1 wherein said keypad and said membrane switch define independent first and second operating stations, each of said first and second operating stations being configured to control two independent power-driven functions of the medical apparatus in response to selective pressure applied on said keypad by a user's foot.

4. The foot control of claim 3 wherein said first operating station is configured to control first and second reversible power-driven functions of the medical apparatus and said second operating station is configured to control third and fourth reversible power-driven functions of the medical apparatus.

5. A foot control for use with medical apparatus having multiple power-driven functions to position a patient supported thereupon in multiple work positions, comprising:
   a base adapted to be supported on a surface;
   a plurality of switch elements supported by said base, each of said switch elements being operable, when actuated, to control at least one of the power-driven functions of the medical apparatus; and
   a plurality of interchangeable flexible keypads, each of said keypads being configured, in an operative position, to overlie said plurality of switch elements and further being uniquely configured to actuate said switch elements in response to selective pressure applied on said keypad by a user's foot so that one of said keypads is configured, in its operative position, to actuate each of said switch elements and the other of said keypads is configured, in its operative position, to actuate less than each of said switch elements.

6. The foot control of claim 5 wherein said plurality of switch elements comprise a membrane switch.

7. The foot control of claim 5 wherein each of interchangeable keypads has, in its operative position, a plurality of switch actuators extending from said keypad toward said switch elements, each of said switch actuators being generally in registry with a respective one of said plurality of switch elements to actuate said switch element in response to selective pressure applied on said keypad by a user's foot.

8. The foot control of claim 7 wherein each of said interchangeable keypads and said plurality of switch actuators are integrally molded from a flexible material.

9. The foot control of claim 5 wherein each of said interchangeable keypads is configured to simultaneously actuate a pair of said switch elements in response to selective pressure applied on said keypad by a user's foot so as to simultaneously control two independent power-driven functions of the medical apparatus upon actuation of said pair of switch elements.

10. The foot control of claim 5 wherein each of said interchangeable keypads and said switch elements define independent first and second operating stations, each of said first and second operating stations being configured to control two independent power-driven functions of the medical apparatus in response to selective pressure applied on said keypad by a user's foot.

11. The foot control of claim 10 wherein said first operating station is configured to control first and second reversible power-driven functions of the medical apparatus and said second operating station is configured to control third and fourth reversible power-driven functions of the medical apparatus.

12. A foot control for use with medical apparatus having multiple power-driven functions to position a patient supported thereupon between a generally upright sitting position and a work position, comprising:
  a base adapted to be supported on a surface;
  a plurality of switch elements supported by said base, each of said switch elements being operable, when actuated, to control at least one of the power-driven functions of the medical apparatus; and
  a flexible keypad overlying said membrane switch and having a plurality of switch actuators extending from said keypad toward said membrane switch, each of said switch actuators being generally in registry with a respective one of said plurality of switch elements to actuate said switch element in response to selective pressure applied on said keypad by a user's foot;
  one of said switch elements being non-programmable and operable, when actuated, to simultaneously control multiple power-driven functions of the medical apparatus to position a patient supported thereupon from the work position to the generally upright sitting position.

13. The foot control of claim 12 wherein said plurality of switch elements comprise a membrane switch.

14. The foot control of claim 12 wherein said keypad and said plurality of switch actuators are integrally molded from a flexible material.

15. The foot control of claim 12 wherein said keypad is configured to simultaneously actuate a pair of said switch elements in response to selective pressure applied on said keypad by a user's foot so as to simultaneously control two independent power-driven functions of the medical apparatus upon actuation of said pair of switch elements.

16. The foot control of claim 12 wherein said keypad and said switch elements define independent first and second operating stations, each of said first and second operating stations being configured to control two independent power-driven functions of the medical apparatus in response to selective pressure applied on said keypad by a user's foot.

17. The foot control of claim 16 wherein said first operating station is configured to control first and second reversible power-driven functions of the medical apparatus and said second operating station is configured to control third and fourth reversible power-driven functions of the medical apparatus.

18. A foot control for use with medical apparatus having multiple power-driven functions to position a patient supported thereupon in multiple work positions, comprising:
  a base adapted to be supported on a surface;
  a plurality of switch elements supported by said base, each of said switch elements being operable, when actuated, to control at least one of the power-driven functions of the medical apparatus; and
  a flexible keypad overlying said plurality of switch elements and being configured to actuate said switch elements in response to selective pressure applied on said keypad by a user's foot;
  said keypad and said switch elements defining independent first and second operating stations, each of said first and second operating stations being configured to control two independent power-driven functions of the medical apparatus in response to selective pressure applied on said keypad by a user's foot,
  wherein said first operating station is configured to control first and second reversible power-driven functions of the medical apparatus and said second operating station is configured to control third and fourth reversible power-driven functions of the medical apparatus.

19. The foot control of claim 18 wherein said switch elements defining said first operating station are aligned on a first axis and a transverse second axis.

20. The foot control of claim 19 wherein said switch elements defining said second operating station are aligned on a third axis and a transverse fourth axis.

21. The foot control of claim 20 wherein said foot control has a central axis and said first and third axes are aligned to intersect said central axis.

22. An examination table, comprising:
  a plurality of support surfaces operable to support a patient in multiple work positions;
  a plurality of actuators operatively connected to said support surfaces and having power-driven functions to position the patient in the multiple work positions; and
  a foot control according to claim 1 operatively coupled to said actuators to control the power-driven functions of said actuators.

23. An examination table, comprising:
  a plurality of support surfaces operable to support a patient in multiple work positions;
  a plurality of actuators operatively connected to said support surfaces and having power-driven functions to position the patient in the multiple work positions; and
  a foot control according to claim 5 operatively coupled to said actuators to control the power-driven functions of said actuators.

24. An examination table, comprising:
  a plurality of support surfaces operable to support a patient in multiple work positions;
  a plurality of actuators operatively connected to said support surfaces and having power-driven functions to position the patient in the multiple work positions; and
  a foot control according to claim 12 operatively coupled to said actuators to control the power-driven functions of said actuators.

25. An examination table, comprising:
  a plurality of support surfaces operable to support a patient in multiple work positions;
  a plurality of actuators operatively connected to said support surfaces and having power-driven functions to position the patient in the multiple work positions; and
  a foot control according to claim 18 operatively coupled to said actuators to control the power-driven functions of said actuators.

26. A foot control for use with medical apparatus having multiple power-driven functions to position a patient supported thereupon in multiple work positions, comprising:
  a base adapted to be supported on a surface;
  a plurality of actuation devices supported by said base, each of said actuation devices being operable, when actuated, to control at least one of the power-driven functions of the medical apparatus; and
  a plurality of foot members connected to said base and adapted to contact the surface upon which said base is supported, each of said foot members comprising an outer head portion, a flange portion and a stem portion extending between the outer head portion and the flange portion.

27. The foot control of claim 26 wherein said base includes a first base member having a plurality of apertures formed therein, each of said foot members being mounted within a respective one of said apertures.

28. The foot control of claim 27 wherein said stem portion of each of said foot members extends through a respective one of said apertures.

29. The foot control of claim 28 wherein said outer head portion and said flange portion of each of said foot members have respective diameters which are greater than a diameter of said apertures.

30. The foot control of claim 29 further comprising a second base member positioned relative to said first base member so as to engage said flange portions of said foot members therebetween.

\* \* \* \* \*